United States Patent [19]

Traenckner et al.

[11] Patent Number: 6,147,238

[45] Date of Patent: Nov. 14, 2000

[54] PROCESS FOR THE PREPARATION OF OCTA-2,7-DIENYL-1-AMINE FROM BUTADIENE AND AMMONIA IN THE PRESENCE OF PALLADIUM COMPLEX CATALYST

[75] Inventors: Hans-Joachim Traenckner, Bergisch Gladbach; Jörg-Dietrich Jentsch, Krefeld; Thomas Prinz, Köln; Birgit Driessen-Hölscher, Aachen; Wilhelm Keim, Aachen, all of Germany

[73] Assignee: Bayer Aktiengesellschaft, Leverkusen, Germany

[21] Appl. No.: 09/512,532

[22] Filed: Feb. 24, 2000

Related U.S. Application Data

[62] Division of application No. 09/257,801, Feb. 25, 1999, Pat. No. 6,051,738.

[30] Foreign Application Priority Data

Feb. 27, 1998 [DE] Germany .......................... 198 08 260

[51] Int. Cl.[7] .............................. C07F 9/02; C07F 15/00; C07C 209/04
[52] U.S. Cl. .............................. 556/21; 556/136; 564/485
[58] Field of Search ........................ 556/21, 136; 564/485

[56] References Cited

U.S. PATENT DOCUMENTS

| | | |
|---|---|---|
| 4,130,590 | 12/1978 | Hobbs et al. ........................ 260/585 D |
| 5,756,846 | 5/1998 | Driessen-Holscher et al. ........ 564/485 |
| 5,834,611 | 11/1998 | Driessen-Holscher et al. .......... 556/21 |

OTHER PUBLICATIONS

Agnew, Chemie, 107, 893 (month unavailable) 1995.
J. Prakt Chem. 335, 591 (month unavailable) 1994.

*Primary Examiner*—Porfirio Nazario-Gonzalez
*Attorney, Agent, or Firm*—Joseph C. Gil; Diderico Van Eyl

[57] ABSTRACT

Process for the preparation of octa-2,7-dienyl-1-amine by telomerization of butadiene with ammonia in a two-phase system in the presence of hydrophilic palladium complexes, characterized in that octa-2,7-dienyl-1-amine and octa-1,7-dienyl-3-amine are isolated separately from one another from the reaction mixture present after telomerization, and the octa-1,7-dienyl-3-amine isolated in this way is subjected to an isomerization reaction to form octa-2,7-dienyl-1-amine, and also novel triphenylphosphine mono- and dimethoxytri(sodium sulphonates) and the use of triphenylphosphine trimethoxytri(sodium sulphonates), triphenylphosphine trimethyltri(sodium sulphonates) and triphenylphosphine trifluorodi- and tri(sodium sulphonates) as ligands for the preparation of palladium complexes.

5 Claims, No Drawings

PROCESS FOR THE PREPARATION OF OCTA-2,7-DIENYL-1-AMINE FROM BUTADIENE AND AMMONIA IN THE PRESENCE OF PALLADIUM COMPLEX CATALYST

This is a divisional application of U.S. Ser. No. 09/257,801, filed Feb. 25, 1999 now U.S. Pat. No. 6,051,738.

FIELD OF THE INVENTION

The present invention relates to an improved process for the preparation of octa-2,7-dienyl-1-amine by telomerization of butadiene with ammonia in a two-phase system, subsequent isolation of octa-2,7-dienyl-1-amine and octa-1,7-dienyl-3-amine from the reaction mixture and isomerization of the octa-1,7-dienyl-3-amine to give octa-2,7-dienyl-1-amine. The present invention further relates to novel triphenylphosphine mono- and dimethoxytri(sodium sulphonates) and to the use of triphenylphosphine trimethoxytri(sodium sulphonates), triphenylphosphine trimethyltri(sodium sulphonates) and triphenylphosphine trifluorodi- and tri(sodium sulphonates) as ligands for the preparation of palladium complexes.

BACKGROUND OF THE INVENTION

Octadienylamines are used, for example, as intermediates for the preparation of octylamines, which in turn are required, for example, for the preparation of fabric softeners, corrosion inhibitors, flotation auxiliaries and emulsifiers. For these purposes, octa-2,7-dienyl-1-amine in particular is of interest.

In the telomerization of butadiene and ammonia, complex reaction mixtures are usually produced which, in addition to octa-2,7-dienyl-1-amine, contain considerable amounts of octa-1,7-dienyl-3-amine and secondary and tertiary octadienylamines.

From EP-A 773 211, it is known to carry out the telomerization of butadiene and ammonia in a two-phase system and to use as catalysts mixtures of palladium compounds and phosphors compounds which improve the solubility of the palladium compounds in water, for example sulphonated triphenylphosphines.

Reaction mixtures containing octa-2,7-dienyl-1-amine (1), octa-1,7-dienyl-3-amine (2) and secondary octadienylamines (3) are produced. (1) forms in selectivities of from 40 to 56%, (2) in selectivities of from 28 to 43% and (3) in selectivities of up to 10%. The reaction mixtures were not worked up.

According to EP-A 816 308, the complex compounds used as catalysts for said telomerization contain, as central atom, a transition metal and at least one tris(hydroxyalkyl)-phosphine or -phosphine oxide as ligand. For butadiene conversions of from 4 to 63%, the selectivity of the formation of (1) can be increased to 66%, and for butadiene conversions below 2% (i.e. large butadiene excesses) up to as much as 85%. The selectivity of the formation of (2) is in the range from 1 to 40%, there being no direct relation of selectivities of the formation of (1) and (2). For example, (2) is obtained with a selectivity of 9% when (1) is produced with a selectivity of 85%, and a selectivity of 1% when (1) is formed with a selectivity of 55%. The reaction mixtures are not worked up here either.

There is therefore a continued need for a process for preparing octa-2,7-dienyl-1-amine in good selectivities and yields as far as possible irrespective of the catalysts, butadiene excesses and other parameters used.

SUMMARY OF THE INVENTION

We have now found a process for the preparation of octa-2,7-dienyl-1-amine by telomerization of butadiene with ammonia in a two-phase system in the presence of hydrophilic palladium catalysts, which is characterized in that octa-2,7-dienyl-1-amine and octa-1,7-dienyl-3-amine are isolated separately from one another from the reaction mixture present after telomerization, and the octa-1,7-dienyl-3-amine isolated in this way is subjected to an isomerization reaction to form octa-2,7-dienyl-1-amine.

DETAILED DESCRIPTION OF THE INVENTION

Ammonia can be used in any desired form. Preference is given to using mixtures of ammonia and water, for example from 5 to 35% by weight strength aqueous ammonia solutions, or pure ammonia (commercially available product).

The two-phase system generally consists of a hydrophilic and a hydrophobic phase. The hydrophilic phase may contain, as essential component, for example water or a hydrophilic solvent or a mixture of hydrophilic solvent and water. The hydrophilic solvent may, for example be $C_1$–$C_6$-mono-, di-, tri-, tetra-, penta- and hexaalcohols, tetramethylene sulphone, dimethyl sulphoxide or acetonitrile. The hydrophilic phase is preferably water which can be used, for example, as such and/or in the form of aqueous solutions of ammonia.

The hydrophobic phase can comprise, as essential component, excess butadiene and/or an organic solvent which is immiscible or virtually immiscible with water. Suitable organic solvents which are immiscible or virtually immiscible with water are, for example, those which, at 20° C., dissolve in 100 g of water only in amounts less than 5 g, in particular less than 3 g. Examples of such solvents are chlorinated aliphatic and aromatic hydrocarbons, ethers, tert-amines, pyrrolidone and aliphatic and aromatic hydrocarbons which are liquid under the reaction conditions. The hydrophobic phase is preferably butadiene, benzene, toluene or methylene chloride, in particular butadiene.

If it is desired to use butadiene as a reactant and as essential component of the hydrophobic phase, it can be used (based on 1 mol of ammonia) in amounts of at least 0.5 mol, for example. This amount is preferably from 0.7 to 100 mol, in particular from 3 to 50 mol. If butadiene is only used as reactant, it can be used (based on 1 mol of ammonia) in amounts of from 0.5 to 20 mol, preferably from 0.7 to 5 mol, for example.

Suitable hydrophilic palladium complexes are, for example, those of the formula (I)

$$[L^1{}_x L^2{}_y Pd]_m p + [A]_n q- \qquad (I),$$

in which
  $L^1$ are identical or different ligands from the group consisting of a sulphonated, carboxylated and hydroxylated trialkyl- and triphenylphosphines and -phosphine oxides, $L^2$ are identical or different ligands from the group consisting of H, CO, NO, $NF_2$, $NH_3$, $PF_3$, $H_2O$, S, halogens, aromatic ligands, olefinic ligands, allylic ligands and acetylenic ligands, x is an integer from zero to 6, and y is zero or an integer from 1 to 5, the sum x+y being at least 1 and at most 6, and m is 1, 2 or 3 and n, p and q are in each case zero, 1, 2 or 3, the relationship m·p=n·q being applicable, and A is an anion with charge q.

Suitable ligands $L^1$ are preferably, mono-, bis- and tri (hydroxy-$C_1$–$C_5$-alkyl)-phosphines, mono-, bis- and tri (hydroxy-$C_1$–$C_5$-alkyl)-phosphine oxides, mono-, di- and trisulphonated triphenylphosphines in acid form and mono-, di- and trisulphonated triphenylphosphines in salt form. In particular, sulphonated triphenylphosphine ligands may also contain further suibstituents on the phenyl rings, for example, per triphenylphosphine unit, from 1 to 3 identical or different halogen atoms and/or from 1 to 3 identical or different $C_1$–$C_{10}$-alkyl groups and/or from 1 to 3 identical or different $C_1$–$C_{10}$-alkoxy groups.

Particularly preferred ligands $L^1$ are tri(hydroxy-$C_1$–$C_5$-alkyl)-phosphines having a terminal arrangement of the hydroxyl groups on the alkyl radicals, triphenylphosphine trisulphonic acids and salts thereof, and triphenylphosphine mono-, di- and trimethoxytri(sodium sulphonic acids) and salts thereof, and triphenylphosphine mono-, di- and trifluoromono-, di- and trisulphonic acids and salts thereof.

Alkyl groups of triphenylphosphine units preferably contain $C_1$–$C_4$-alkyl radicals and alkoxy groups present there, preferably $C_1$–$C_4$-alkoxy radicals.

Very particularly preferred ligands $L^1$ are tris(hydroxy-3-propyl)-phosphine and the trisodium salt of 3,3',3"-phosphinetriyl-tris-(benzenesulphonic acid), called TPPTS below, the trisodium salt of 3,3',3"-phosphinetriyl-bis-(benzenesulphonic acid)-mono(4-methoxybenzenesulphonic acid), called MOM-TPPTS below, the trisodium salt of 3,3',3"-phosphinetriyl mono (benzenesulphonic acid)-bis-(4-methoxybenzenesulphonic acid), called BOM-TPPTS below, the trisodium salt of 3,3',3"-phosphinetriyl-tris(4-methoxybenzenesulphonic acid), called TOM-TPPTS below, the trisodium salt of 3,3',3"-phosphinetriyl-tris-(4-methylbenzenesulphonic acid), called TOT-TPPTS below, the trisodium salt of 5,5', 5"-phosphinetriyl-tris-(2-fluorobenzenesulphonic acid), called p-F-TPPTS below, and the disodium salt of 5,5'-(4-fluorophenylphosphinediyl)-bis-(2-fluorobenzenesulphonic acid), called p-F-TPPDS below.

Suitable ligands $L^2$ are, preferably, $NH_2$, $NH_3$, Cl, Br, I, allyl, methallyl, cyclopentadienyl, cyclooctadienyl and dibenzylideneacetone.

In formula (I), x is preferably zero or an integer from 1 to 4, in particular an integer front 1 to 4, and y is preferably zero, 1 or 2, the sum x+y being at most 4.

The anion A is preferably acetate, chloride, acetylacetonate, tetrafluoroborate and hexafluoroantimonate.

MOM-TPPTS and BOM-TPPTS are novel compounds. These conform in particular to the formulae (II) and (III)

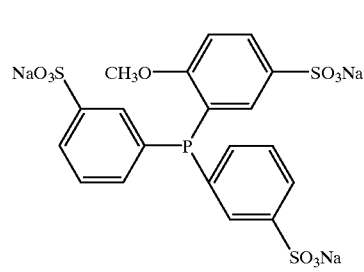

(II)

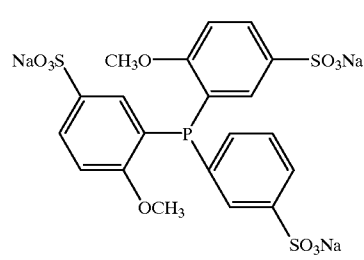

(III)

and are also provided by the present invention. They can be prepared as described in Angew. Chemie 107, 893 (1995).

The use of TOM-TPPTS, TOT-TPPTS, p-F-TPPTS and p-F-TPPDS as ligand for the preparation of palladium complexes for the telomerization of butadiene with ammonia is also novel and provided by the present invention. Such compounds can be prepared as described in Angew. Chemie 107, 893 (1995) or J. prakt. Chem. 336, 591, (1994).

The preparation of the hydrophilic palladium complexes of the formula (I) can be carried out in a simple manner, for example by adding ligands of type $L^1$ and/or of type $L^2$ to an initial charge of a palladium salt or a palladium complex compound and water. This then gives an aqueous solution of the hydrophilic palladium complex of the formula (I), which can be used as such in the process according to the invention, it is, however, also possible to isolate the corresponding complexes of the formula (I) and then use the isolated complexes in the process according to the invention.

It is also possible to prepare hydrophilic palladium complexes of the formula (I) in situ, for example by initially introducing a palladium salt or a palladium complex compound together with water or aqueous ammonia solution into an autoclave, then addling butadiene, the desired ligands and optionally further aqueous ammonia solution and then setting the pressure and temperature conditions desired for the telomerization. In this case, it is possible, for example, to use 0.1–50 mol of the desired ligand per mole of palladium salt or palladium complex compound used. This amount is preferably 0.2–30 mol, in particular 0.3–10 mol. In the in-situ preparation of complexes of the formula (I), mixtures of different individual substances of the formula (I) may also form, which are then effective, even in the form of such mixtures, as catalysts for the process according to the invention.

Starting compounds for the preparation of hydrophilic palladium complexes which are to be used according to the invention are, for example, the following palladium salts and complexes: palladium(II) acetate, chloride, acetylacetonate, hexafluoroantimonate and tetrafluoroborate, and allyldiaminopalladium(II) tetrafluoroborate, bis-(η3-allyliodo)-palladium(II), allyldiaminopalladium(II) hexafluoroantimonate and any other palladium(II) salts or complexes of this type. The choice of palladium salts or complexes for the preparation of hydrophilic palladium complexes of the formula (I) is of no particular significance for the process according to the invention. The starting compounds for the preparation of hydrophilic palladium) complexes to be used according to the invention are also palladium(0) complexes, e.g. those of the formula

$$PdL^1_{x'} \qquad (IV)$$

in which
L$^1$ is as defined for formula (I), and
x' is an integer from 1 to 6,
or palladium dibenzylideneacetone.

It is also possible that the oxidation stage of the hydrophilic palladium complex changes whilst the process according to the invention is being carried out.

Per litre of hydrophilic phase, it is possible to use, for example, from 0.5 to 500 millimol of hydrophilic palladium complexes. This amount is preferably from 1 to 25 millimol, in particular from 2.5 to 10 millimol. If the hydrophilic palladium complexes are prepared in situ, then, for example, from 0.5 to 500 millimol of palladium salt or palladium complex compound are used per litre of hydrophilic phase. This amount is preferably from 1 to 25 millimol, in particular from 2.5 to 10 millimol.

The use of catalysts of the formula (I) in which L$^1$ is a compound of the formula (II) or (III) or is TOM-TPPTS or TOT-TPPTS gives reaction mixtures which contain relatively high contents of octa-2,7-dienyl-1-amine. It is, however, also possible to obtain even more octa-2,7-dienyl-1-amine if the octa-1,7-dienyl-3-amine also obtained, in relatively small amounts, is isolated and isomerized to give octa-2,7-dienyl-1-amine. The use of catalysts of the formula (I) in which L$^1$ is p-F-TPPTS and p-F-TPPDS generally leads to an increased activity of the catalyst.

The telomerization reaction of butadiene with ammonia can be carried out, for example, at temperatures in the range from 30 to 150° C. and pressures in the range from 1 to 30 bar. The reaction is preferably carried out at from 50 to 120° C. and in an autoclave under the autogenous pressure at the corresponding reaction temperature.

The telomerization reaction is generally complete after from 30 minutes to 20 hours. It is advantageous to ensure that the reaction mixture is thoroughly mixed during the reaction.

The reaction mixture can be worked up and the octa-2,7-dienyl-1-amine and octa-1,7-dienyl-3-amine present therein isolated separately as follows, for example:

If butadiene has been used as essential constituent of the hydrophobic phase, then butadiene which is present in excess escapes when the system is decompressed to atmospheric pressure. Residual butadiene which remains in the reaction mixture can, if necessary, be blown out, e.g. with nitrogen. This then gives an aqueous phase containing the catalyst and an organic phase containing the reaction products, which can be worked up, following separation, as described below. It is advantageous to extract the hydrophilic phase with a suitable solvent, and then to add the extracted phase to the hydrophobic phase for combined work-up.

If an organic solvent has been used to form the hydrophobic phase, the hydrophobic phase can be separated from the hydrophilic phase, and the separated-off hydrophilic phase can, if necessary, be washed with a water-immiscible solvent, and the wash liquid added to the hydrophobic phase.

The hydrophilic phase containing the catalyst can be used as desired, e.g. in the next batch for the preparation according to the invention of octa-2,7-dienyl-1-amine (1) or for the isomerization of isolated octa-1,7-dienyl-3-amine (2).

It is possible to subject the hydrophobic phase, if necessary after the solvent present has been stripped off, and if necessary after a free-radical scavenger (e.g. a sterically hindered phenol) has been added, to fractional distillation. At pressures of, for example, from 4 to 40 mbar, the boiling points of (1) and (2) are sufficiently different from each other to allow them to be readily separated from one another in columns having, for example, from 50 to 150 theoretical plates and at reflux ratios of, for example, 3:1 to 15:1. In this way, it is possible to obtain a first fraction which contains (2) and a second fraction which contains (1), each in purities up to 99% and above. The substances which remain are relatively high boiling constituents, in particular bis-octadienylamines.

Up to this process step, it is possible to obtain (1) in selectivities (based on reacted butadiene) of, for example, from 40 to 87% and (2) in selectivities (based on reacted butadiene) of, for example, from 7 to 40%.

According to the invention, the selectivity of the formation of (1) is then increased by, for example, from 1 to 25% (based on the original selectivity) when (2) obtained as described above is subjected to an isomerization reaction to form (1).

This isomerization can be carried out in analogous manner to the telomerization described above, i.e. using the same catalyst and in a two-phase system. For the isomerization, it is advantageous to use the catalyst, or solution thereof, separated off during work-up of the telomerization mixture. In contrast to the parameters given above for the telomerization, it is advantageous to carry out the isomerization under the following conditions:

Per litre of hydrophilic phase, it is possible to use, for example, from 0.5 to 500 millimol of hydrophilic palladium complexes. This amount is preferably from 1 to 25 millimol, in particular from 2.5 to 10 millimol. It is also possible to use the hydrophilic palladium complexes in situ, for example by initially introducing a palladium salt or a palladium complex compound together with water or an aqueous ammonia solution and adding the desired ligand. In this case, it is possible to use, for example, from 0.5 to 500 millimol of palladium salt or palladium complex per litre of hydrophilic phase. This amount is preferably from 1 to 25 millimol, in particular from 2.5 to 10 millimol. Per mole of palladium salt or palladium complex compound used, it is possible to use 0.1–50 mol of the desired ligand. This amount is preferably 0.2–30 mol, in particular from 0.3 to 10 mol.

The essential component of the hydrophilic phase can, for example, be water or a hydrophilic solvent or ammonia. It is also possible to use any desired mixtures of water, hydrophilic solvents and ammonia. The presence of ammonia is always preferable. The hydrophilic solvents are, for example, $C_1$–$C_6$ mono-, di-, tri-, tetra-, penta- and hexaalcohols, tetramethylenesulphone, dimethyl sulphoxide or acetonitrile. The hydrophilic phase is preferably water, ammonia and mixtures of water and ammonia having an ammonia content of from 1 to 99% by weight. Particular preference is given to an ammonia content of from 5 to 60% by weight. Very particularly preferably, the ammonia content is from 10 to 30% by weight. Per litre of hydrophilic phase, it is possible to use, for example, from 10 to 5000 g of octa-1,7-dienyl-3-amine (2). Preference is given to using from 50 to 3000 g, and particular preference to from 100 to 2000 g, of octa-1,7-dienyl-3-amine.

The temperature is, for example, from 20 to 200° C., preferably from 40 to 150° C. and particularly preferably from 60 to 120° C.

The pressure is for example, from 0 to 500 bar. The process is preferably carried out at a pressure of from 0 to 100 bar, particularly preferably at the pressure which automatically results at the particular temperature. It is also possible to carry out the reaction in an apparatus in which atmospheric pressure prevails as a result of pressure compensation with the surroundings.

The reaction time is generally from 1 hour to 14 days and depends on the ratio of octa-1,7-dienyl-3-amine (2) relative to the palladium salt or palladium complex used and the desired degree of isomerization. It is advantageous to ensure that the reaction mixture is thoroughly mixed during the reaction.

The reaction mixture which remains when isomerization is complete can be worked up in the same way as the reaction mixture which remains following telomerization, for example by phase separation, extraction of the aqueous phase by an organic solvent and subsequent distillation of the combined organic phases.

It is also possible to carry out the isomerization several times successively with the (2) separated off from the preceding stage in each case.

The invention is further described in the following illustrative examples. All percentages are by weight, unless otherwise noted.

EXAMPLES

Example 1

4.38 g of boric acid are dissolved completely in 41 ml of concentrated sulphuric acid in a 500 ml three-necked flask under an argon atmosphere (argon is passed through the sulphuric acid beforehand in order to free it from oxygen). 5 g of (orthomethoxyphenyl)diphenylphosphine are then dissolved therein, and the mixture is cooled to –10° C. with an ice/sodium chloride mixture. At this temperature, 73.9 ml of oleum are added dropwise over a period of 2 h, and the solution is then stirred for 3 h at room temperature.

Before the synthesis is continued with the hydrolysis, a 5 ml sample is firstly taken and worked up in the same way as is described below for the entire mixture. A $^{31}$P-NMR spectroscopic investigation of this sample provides information as to whether the sulphonation has already proceeded to completion. If the reaction times are too short, mono- and disulphonated product is still present, and if the reaction times are too long, phosphine oxide is present. These impurities are as a whole very difficult to remove.

For hydrolysis, 50 ml of oxygen-free water are added very slowly with ice cooling. The mixture is then transferred to a 2 l Schlenk flask and neutralized there with 7.5 molar sodium hydroxide solution with ice cooling. It is advisable to adjust the pH to 7 as accurately as possible using a pH electrode. The solution is then evaporated to dryness on a rotary evaporator, and then the product is extracted with 250 ml of methanol. The solution is filtered over Celite®, and methanol is distilled off under reduced pressure. The residue is taken up in 20 ml of water and the mixture is filtered through a syringe filter, and the water is removed under reduced pressure. Alternating extraction with methanol and water gives MOM-TPPTS as trihydrate in a purity of 93% and a yield of 14%.

$^{31}$-NMR (D$_2$O): –14.6 ppm; $^1$H-NMR (D$_2$O): 3.6 ppm (3H); 6.96 ppm (1H); 7.02 ppm (1H); 7.3 ppm (2H); 7.4 ppm (2H); 7.6 ppm (2H); 7.7 ppm (3H); $^{13}$C-NMR (D$_2$O): 164.2 ppm; 144.6 ppm; 138.1 ppm; 137.06 ppm; 137.1 ppm; 132.25 ppm; 131.9 ppm; 131.2 ppm; 130.8 ppm; 128.2 ppm; 125.7 ppm; 112.9 ppm; 57.7 ppm.

Example 2

The synthesis of BOM-TPPTS is carried out in an entirely analogous manner as described in Example 1, but using bis(ortho-methoxyphenyl)-phenylphosphine instead of (ortho-methoxyphenyl)diphenylphosphite. BOM-TPPTS is obtained as the trihydrate in 92% purity with a yield of 14%.

$^{31}$-NMR (D$_2$O): –24.34 ppm; $^1$H-NMR (D$_2$O): 3.6 ppm (6H); 7.0 ppm (2H); 7.03 ppm (2H); 7.3 ppm (1H); 7.4 ppm (1H); 7.6 ppm (1H); 7.7 ppm (3H); $^{13}$C-NMR (D$_2$O): 161.7 ppm; 141.9 ppm; 135.5 ppm; 134.4 ppm; 133.55 ppm; 129.6 ppm; 129.4 ppm; 128.5 ppm; 128 ppm; 125.6 ppm; 121.8 ppm; 110.3 ppm; 55 ppm.

Example 3

1372 mg of bis($^3$η-allyl-iodopalladium) are dissolved in 10 ml of an aqueous 27% strength NH$_3$ solution. This solution is added to a solution of 973.4 mg of AgBF$_4$ in 5 ml of water. The AgI which precipitates out is then filtered off over Celite®. The filtrate is reduced by evaporation, and the product is dissolved out of the residue by triple extraction with 10 ml of boiling CH$_2$Cl$_2$ in each case, and this solution is in each case decanted off. Some of the product precipitates out merely upon cooling, and the remainder is precipitated out by adding 20 ml of pentane. The white solid is washed three times with 5 ml of pentane in each case and dried under a high vacuum.

[$^3$η-Allyl-diaminopalladium]tetrafluoroborate is obtained in a yield of 50.3%.

$^1$H-NMR (D$_2$O): 2.9 ppm (2H); 4.0 ppm (2H); 5.5 ppm (1H); $^{13}$C-NMR (D$_2$O): 61 ppm; 118 ppm.

Example 4

The reaction is carried out in a stainless steel autoclave having a volume of 125 ml which contains a stirring system comprising a 6-blade disc agitator in combination with flow disruptors, and is heated electrically. The autoclave is initially assembled, and evacuated three times to remove the oxygen and filled with argon.

30.3 mg of [$^3\eta$-allyl-diaminopalladium]tetrafluoroborate are weighed into a Schlenk tube and, together with 15 ml of an aqueous 27% strength ammonia solution, transferred to the autoclave. 40 g of butadiene are then introduced via a metering cartridge. The contents of the reactor are heated to 80° C. with stirring (2000 rpm). Meanwhile, 0.113 mmol of TPPTS in the form of a 32.4% aqueous solution are weighed into a Schlenk tube and, together with 15 ml of an aqueous ammonia solution, transferred to a steel dropping funnel. The latter is assembled on the autoclave. At an internal temperature of 80° C., the pressure compensation is firstly opened, followed by the tap of the dropping funnel. The temperature drops to about 60° C., but within 3 min again reaches the desired value of 80° C. After a reaction time of 45 min, the autoclave is placed into an icebath and, with the speed of the stirrer reduced (200 rpm), the excess butadiene is blown off using a Bunsen burner. In this way, the contents of the reactor cool to 20° C. over the course of 5 min. When all of the butadiene has been burned off, the autoclave is opened and the contents transferred to a separating funnel. Rinsing is then carried out with 10 ml of toluene, followed by extraction, and a spatula tip of sodium chloride is added to accelerate phase separation. Following phase separation, the GC standard undecane is weighed into the organic phase, which is dried over a 4 Å molecular sieve. The molecular sieve is then filtered off and washed with 10 ml of toluene. A sample is taken, and the composition is investigated using gas chromatography. The conversion in terms of butadiene was 5.8%. The composition of the sample was 76% of (1), 21% of (2) and 3% of (3).

Examples 5 to 7

The procedure is identical to that described in Example 4. However, instead of 0.113 mmol of TPPTS, other amounts of this compound are used. The examples are listed in Table 1:

TABLE 1

| Example No. | Amount of TPPTS | Conversion (based on butadiene) | Composition (% by weight) | | |
|---|---|---|---|---|---|
| | | | (1) | (2) | (3) |
| 5 | 0.226 mmol | 15.5% | 50 | 35 | 12 |
| 6 | 0.452 mmol | 7.0% | 51 | 43 | 4 |
| 7 | 0.678 mmol | 0.9% | 48 | 50 | 0.5 |

Examples 8 to 11

The procedure is identical to that described in Example 4. However, instead of an aqueous solution of TPPTS, MOM-TPPTS is used in the form of the trihydrate. The amounts of this compound used are likewise varied. The examples are listed in Table 2:

TABLE 2

| Example No. | Amount of MOM-TPPTS | Conversion (based on butadiene) | Composition (% by weight) | | |
|---|---|---|---|---|---|
| | | | (1) | (2) | (3) |
| 8 | 0.113 mmol | 6% | 70 | 22 | 7 |
| 9 | 0.226 mmol | 16.5% | 49 | 40 | 8 |
| 10 | 0.452 mmol | 13.4% | 40 | 37 | 8 |
| 11 | 0.678 mmol | 5.2% | 42 | 40 | 2.2 |

Examples 12 to 15

The procedure is identical to that described in Example 4. Instead of using an aqueous solution of TPPTS, BOM-TPPTS in the form of its trihydrate is used. The amounts of this compound used are likewise varied. The examples are listed in Table 3:

TABLE 3

| Example No. | Amount of BOM-TPPTS | Conversion (based on butadiene) | Composition (% by weight) | | |
|---|---|---|---|---|---|
| | | | (1) | (2) | (3) |
| 12 | 0.113 mmol | 2.9% | 87 | 7 | 5 |
| 13 | 0.226 mmol | 6.5% | 65 | 17 | 0.3 |
| 14 | 0.452 mmol | 8.0% | 58 | 33 | 7 |
| 15 | 0.678 mmol | 9.3% | 53 | 33 | 7 |

Examples 16 to 19

The procedure is identical to that described in Example 4. Instead of using an aqueous solution of TPPTS, TOM-TPPTS in the form of its trihydrate is used. The amounts of this compound used are likewise varied. The examples are listed in Table 4:

TABLE 4

| Example No. | Amount of TOM-TPPTS | Conversion (based on butadiene) | Composition (% by weight) | | |
|---|---|---|---|---|---|
| | | | (1) | (2) | (3) |
| 16 | 0.113 mmol | 1.05% | 94 | 3 | 1 |
| 17 | 0.226 mmol | 2.25% | 94 | 3.5 | 1.2 |
| 18 | 0.452 mmol | 2.3% | 87 | 4 | 3 |
| 19 | 0.678 mmol | 2.3% | 89 | 7 | 3 |

Examples 20 to 22

The procedure is identical to that described in Example 4. However, instead of using an aqueous solution of TPPTS, TOT-TPPTS in the form of its trihydrate is used. The amounts of this compound used are likewise varied. The examples are listed in Table 5:

TABLE 5

| Example No. | Amount of TOT-TPPTS | Conversion (based on butadiene) | Composition (% by weight) | | |
|---|---|---|---|---|---|
| | | | (1) | (2) | (3) |
| 20 | 0.113 mmol | 1.05% | 91 | 5 | 1 |
| 21 | 0.339 mmol | 3.3% | 86 | 4 | 8 |
| 22 | 0.678 mmol | 2.7% | 90 | 5 | 3 |

Example 23

The procedure is identical to that described in Example 4. However, instead of using an aqueous solution of TPPTS, 2.428 mmol of TOM-TPPTS in the form of the trihydrate and 0.971 mol of [$^3\eta$-allyl-diaminopalladium] tetrafluoroborate are used. The conversion in terms of butadiene was 29.0%. The composition of the sample is 67% by weight of (1), 13% by weight of (2) and 17% by weight of (3).

Example 24

The procedure is identical to that described in Example 18. However, in this case a reaction time of 7 hours is maintained. The conversion in terms of butadiene was 30.4%. The composition of the sample is 78% by weight of (1), 5% by weight of (2) and 16% by weight of (3).

Example 25

The procedure is identical to that described in Example 4. However, instead of using an aqueous solution of TPPTS, a mixture of 0.099 mmol of p-F-TPPDS in the form of the dihydrate and 0.015 mmol of p-F-TPPTS in the form of the trihydrate is used. The conversion in terms of butadiene was 8.2%. The composition of the sample is 54% by weight of (1), 38% by weight of (2) and 6% by weight of (3).

Examples 26 to 29

The procedure is identical to that described in Example 4. However, instead of [$^3\eta$-allyl-diaminopalladium] tetrafluoroborate, other palladium compounds are used. In addition, the amount of TPPTS used was varied. The examples are listed in Table 6:

TABLE 6

| Example No. | Palladium compound | Amount of TPPTS | Conversion (based on butadiene) | Composition (% by weight) | | |
|---|---|---|---|---|---|---|
| | | | | (1) | (2) | (3) |
| 26 | Palladium acetate | 0.339 mmol | 15.7% | 53 | 35 | 6 |
| 27 | Palladium bis-(diacetyl-acetonate) | 0.339 mmol | 11.3% | 53 | 40 | 6 |
| 28 | Palladium chloride | 0.339 mmol | 14.2% | 54 | 39 | 6 |
| 29 | Bis-($^3\eta$-allyl-iodo-palladium) | 0.226 mmol | 13.5% | 58 | 32 | 9 |

Example 30

A solution of 1.5 mmol of palladium acetate and 4.5 mmol of TPPTS (TPPTS is used in the form of a 32.4% strength aqueous solution) in 250 ml of a 20% strength aqueous ammonia solution is introduced, in an argon counterflow, into a stainless steel autoclave which has been evacuated three times beforehand and filled with argon. 120 g of butadiene are condensed and the autoclave is heated to 80° C. with vigorous stirring over a period of 15 min. The reaction mixture is vigorously mixed at this temperature for a further 45 min. Heating is then stopped and the excess butadiene is burned off using a Bunsen burner. As a result, the contents of the autoclave cool. When all of the butadiene has been burned off, the contents of the autoclave are transferred to a separating funnel and the phases are separated. The aqueous phase is extracted 3 times with 40 ml of pentane in each case, and this extract is combined with the organic phase. The water which is eliminated in the process is separated off and discarded. The residual organic phase is dried over a molecular sieve. The drying agent is separated off and the solvent is removed on a rotary evaporator. The residual liquid is mixed with 2 g of 2,4-di-tert-butylphenol and subjected to fractional distillation. A column with 80 theoretical plates and a reflux ratio of 1:10 is used. At a pressure of 20 mbar and a head temperature of 61° C., 34.1 g of compound (2) are isolated. Likewise at 20 mbar and a head temperature of 75.5° C., 55 g of compound (1) are isolated.

The total amount of compound (2) is transferred for isomerization to a glass autoclave together with 0.974 mmol of palladium acetate, 5.58 mmol of TPPTS (in the form of a 32.4% strength aqueous solution) and 290 ml of a 27% strength ammonia solution. The mixture is stirred vigorously for 15 hours at a temperature of 80° C. and then cooled to room temperature. The phases are separated, the aqueous phase is extracted with a total of 50 ml of pentane, and the extracts are combined with the organic phase. The water which is eliminated is separated off and discarded. The organic phase is dried over a molecular sieve, the drying agent is separated off and the solvent is removed on a rotary evaporator. The residue is, as already described above, subjected to fractional distillation. This gives 19.8 g of compound (2) and 6.5 g of compound (1). The total amount of compound (2) is again subjected to an isomerization reaction and subsequent separation by distillation in a manner which is entirely analogous to that described above. This gives 3.6 g of compound (1) and 11.5 g of compound (2). The total amount of compound (2) is in turn subjected to an isomerization reaction and subsequent separation by distillation in a manner which is entirely analogous to that described above. This gives 1.8 g of compound (1) and 6.1 g of compound (2).

Altogether, the telomerization with subsequent triple isomerization described here gives 66.9 g of compound (1), which corresponds to a conversion of 48.2% in terms of butadiene.

Examples 31 and 32

The experiments for recycling the catalyst phase were carried out in a stainless steel autoclave having a volume of 125 ml, which contains a stirring system comprising a 6-blade disc agitator in combination with flow disruptors and which is heated electrically. The autoclave is initially assembled and evacuated three times to remove the oxygen and filled with argon.

25.4 mg of palladium acetate and the corresponding amount of TPPTS are weighed into a Schlenk tube. The catalyst is transferred to the autoclave together with 30 ml of a 27% strength aqueous $NH_3$ solution. 40 g of butadiene are then condensed, and the autoclave is heated to the reaction temperature (80° C.) with stirring. The heating phase lasts 25 min. After this heating phase, the reaction temperature is maintained for a further 50 min. The autoclave is then placed into an icebath and the butadiene is blown off using a Bunsen burner. As a result, the internal temperature drops to 20° C. within 5 min. When all of the butadiene has been burned off, the contents of the reactor are transferred, via a riser pipe which extends to the floor inside the autoclave, to a protective-gas separating funnel. For this, argon is fed onto the autoclave at a pressure of 0.5 bar via the needle valve, this pressing out the liquid via the riser pipe. In the separating funnel, the phases are separated and the catalyst phase is transferred back to the autoclave. 1 g of ammonia and 40 g of butadiene are then condensed in the autoclave. The procedure from here is the same as that already described for the first run. A total of 4 runs are carried out with the same catalyst phase. The organic phases are admixed with 10 ml of toluene, and the GC standard undecane is weighed in. The phases are then dried over a 4 Å molecular sieve and the composition is determined by gas chromatography. The results are listed in Tables 7 and 9.

TABLE 7

Example 31: 0.339 mmol of TPPTS were used

| | Conversion | Composition (% by weight) | | |
|---|---|---|---|---|
| | (based on butadiene) | (1) | (2) | (3) |
| Run 1 | 17.6% | 55 | 37 | 7 |
| Run 2 | 14.3% | 53 | 36 | 10 |
| Run 3 | 12.9% | 53 | 31 | 15 |
| Run 4 | 5.9% | 54 | 28 | 16 |

TABLE 8

Example 32: 0.565 mmol of TPPTS were used

| | Conversion | Composition (% by weight) | | |
|---|---|---|---|---|
| | (based on butadiene) | (1) | (2) | (3) |
| Run 1 | 4.3% | 50 | 45 | 3 |
| Run 2 | 6.6% | 49 | 43 | 5 |
| Run 3 | 9.2% | 47 | 40 | 8 |
| Run 4 | 8.1% | 46 | 41 | 7 |

Example 33

The procedure is as described in Examples 31 and 32 but using TOM-TPPTS instead of TPPTS. A weighed amount of TOM-TPPTS corresponded to an amount of 0.565 mmol. The reaction time was 200 minutes. The result of the experiment is given in Table 9.

TABLE 9

| | Conversion | Composition (% by weight) | | |
|---|---|---|---|---|
| | (based on butadiene) | (1) | (2) | (3) |
| Run 1 | 7.7% | 88 | 45 | 6.5 |
| Run 2 | 10.7% | 85 | 5 | 10 |
| Run 3 | 9.6% | 77 | 5 | 16 |
| Run 4 | 8.3% | 75 | 5 | 17 |

Although the invention has been described in detail in the forgoing for the purpose of illustration, it is to be understood that such detail is for that purpose and that variations can be made therein by those skilled in the art without departing form the spirit and scope of the invention.

What is claimed is:

1. A method for preparing a hydrophilic palladium complex comprising combining:
   (i) a ligand component comprising a component selected from the group consisting of the trisodium salt of 3,3',3"-phosphinetriyl-bis-(benzenesulphonic acid)-mono-(4-methoxybenzenesulphonic acid), the trisodium salt of 3,3',3"-phosphinetriylmono-(benzenesulphonic acid)-bis(4-methoxy-benzenesulphonic acid), the trisodium salt of 5,5',5"-phosphinetriyl-tris-(2-fluorobenzenesulphonic acid) and the disodium salt of 5,5'-(4-fluorophenylphosphinediyl)-bis-(2-fluorobenzenesulphonic acid); and
   (ii) a palladium complex starting compound, and
   (iii) water.

2. The method of claim 1, wherein the palladium complex starting compound comprises a component selected from the group consisting of palladium(II) acetate, palladium(II) chloride, palladium(II) acetylacetonate, palladium(II) hexafluoroantimonate, palladium(II) tetrafluoroborate, allyldiaminopalladium(II) tetrafluroborate, bis-(η3-allyl-iodo)-palladium(II), allyldiaminopalladium(II) tetrafluroborate, and allyldiaminopalladium(II) hexafluoroantimonate, palladum(O) complexes, and palladium dibenzylideneacetone.

3. A method for preparing a hydrophilic palladium complex in-situ comprising the steps of:
   (a) introducing a palladium complex starting compound and an aqueous component into a vessel,
   (b) adding butadiene into the vessel,
   (c) adding a ligand component comprising a component selected from the group consisting of the trisodium salt of 3,3',3"-phosphinetriyl-bis-(benzenesulphonic acid)-mono-(4-methoxybenzenesulphonic acid), the trisodium salt of 3,3',3"-phosphinetriylmono-(benzenesulphonic acid)-bis(4-methoxy-benzenesulphonic acid), the trisodium salt of 5,5',5"-phosphinetriyl-tris-(2-fluorobenzenesulphonic acid) and the disodium salt of 5,5'-(4-fluorophenylphosphinediyl)-bis-(2-fluorobenzenesulphonic acid).

4. The method of claim 3, wherein the aqueous component comprises a component selected from water and aqueous ammonia solutions.

5. The method of claim 3, wherein the palladium complex starting compound comprises a component selected from the group consisting of palladium(II) acetate, palladium(II) chloride, palladium(II) acetylacetonate, palladium(II) hexafluoroantimonate, palladium(II) tetrafluoroborate, allyldiaminopalladium(II) tetrafluoroborate, bis-(η3-allyl-iodo)-palladium(II), allyldiaminopalladium(II) tetrafluroborate, and allyldiaminopalladium(II) hexafluoroantimonate, palladium(O) complexes, and palladium dibenzylideneacetone.

* * * * *